(12) United States Patent
McCully et al.

(10) Patent No.: US 12,091,651 B2
(45) Date of Patent: Sep. 17, 2024

(54) AUTOMATED ISOLATION OF VIABLE MITOCHONDRIA

(71) Applicant: Children's Medical Center Corporation, Boston, MA (US)

(72) Inventors: James D. McCully, Marblehead, MA (US); Douglas B. Cowan, Brighton, MA (US); Pedro J. Del Nido, Lexington, MA (US); Thomas Duignan, Jamaica Plain, MA (US)

(73) Assignee: Children's Medical Center Corporation, Boston, MA (US)

( * ) Notice: Subject to any disclaimer, the term of this patent is extended or adjusted under 35 U.S.C. 154(b) by 736 days.

(21) Appl. No.: 17/052,709

(22) PCT Filed: May 8, 2019

(86) PCT No.: PCT/US2019/031312
§ 371 (c)(1),
(2) Date: Nov. 3, 2020

(87) PCT Pub. No.: WO2019/217551
PCT Pub. Date: Nov. 14, 2019

(65) Prior Publication Data
US 2021/0238534 A1 Aug. 5, 2021

Related U.S. Application Data

(60) Provisional application No. 62/668,358, filed on May 8, 2018.

(51) Int. Cl.
*C12M 1/36* (2006.01)
*C12M 1/00* (2006.01)
(Continued)

(52) U.S. Cl.
CPC ............ *C12M 41/48* (2013.01); *C12M 33/14* (2013.01); *C12M 41/14* (2013.01); *C12M 47/20* (2013.01);
(Continued)

(58) Field of Classification Search
CPC ...... C12M 41/48; C12M 41/14; C12M 33/14; C12M 47/20; C12M 47/08; G01N 15/042;
(Continued)

(56) References Cited

U.S. PATENT DOCUMENTS 4,969,902 A * 11/1990 Ravo ..................... A61F 2/0009
128/DIG. 25
5,057,432 A 10/1991 Wangersky et al.
(Continued)

FOREIGN PATENT DOCUMENTS

| CN | 105247042 A | 1/2016 |
| CN | 105874319 A | 8/2016 |

(Continued)

OTHER PUBLICATIONS

EP European Search Report in European Appln. No. 19800102.6, dated Jan. 27, 2022, 8 pages.
(Continued)

*Primary Examiner* — Michael L Hobbs
(74) *Attorney, Agent, or Firm* — Fish & Richardson P.C.

(57) ABSTRACT

An automated isolation device for isolation of mitochondria includes an incubation station including a holder for a viable mitochondria solution; and a cooling system, controlled by a processor of the device, for cooling the holder. The device includes a processor-controlled transfer system for transferring solution from the holder to a filtration station; and the filtration station, including a series of filters. The device includes a processor-controlled spectrometry station includ-
(Continued)

ing a spectrometer positioned to illuminate a cuvette fluidically coupled to an output of the filtration station; and a detector coupled to the processor and positioned on a side of the cuvette opposite the spectrometer. The device includes a processor-controlled transfer system for transferring solution from the spectrometry station to a centrifuge. The centrifuge is processor-controlled and configured to centrifuge the filtrate to separate viable mitochondria from a supernatant.

16 Claims, 9 Drawing Sheets

(51) Int. Cl.
*C12M 1/26* (2006.01)
*G01J 3/44* (2006.01)
*G01N 15/04* (2006.01)
*G01N 33/50* (2006.01)
*G01N 35/00* (2006.01)

(52) U.S. Cl.
CPC .............. *G01J 3/44* (2013.01); *G01N 15/042* (2013.01); *G01N 33/5079* (2013.01); *G01N 2035/00356* (2013.01); *G01N 2035/00475* (2013.01); *G01N 2035/00495* (2013.01)

(58) Field of Classification Search
CPC .............. G01N 33/5079; G01N 21/65; G01N 2015/0062; G01N 2035/00356; G01N 2035/00475; G01N 2035/00495; G01J 3/44
See application file for complete search history.

(56) References Cited

U.S. PATENT DOCUMENTS

| 2014/0329244 A1 | 11/2014 | Ding et al. |
| 2016/0139012 A1 | 5/2016 | D'Silva et al. |
| 2017/0120237 A1 | 5/2017 | McCully et al. |

FOREIGN PATENT DOCUMENTS

| CN | 106536056 A | 3/2017 |
| JP | 2011511934 | 4/2011 |
| WO | WO 2006/070752 | 6/2008 |
| WO | WO 2012/178210 | 12/2012 |
| WO | WO 2015051466 | 4/2015 |
| WO | WO 2015/192020 | 12/2015 |
| WO | WO 2016/126314 | 8/2016 |

OTHER PUBLICATIONS

JP Japanese Office Action in Japanese Appln. No. 2020-560492, dated Feb. 8, 2023, 8 pages (with English translation).
PCT International Preliminary Report on Patentability in International Appln. No. PCT/US2019/31312, dated Nov. 10, 2020, 10 pages.
PCT International Search Report and Written Opinion in International Appln. No PCT/US2019/31312, dated Sep. 10, 2019, 18 pages.
Tang et al., "Raman spectroscopic investigation of single mitochondria trapped by optical tweezers," Optics Express, Oct. 1, 2007, 15(20):12708-16.
AU Office Action in Australian Appln. No 2019265630, mailed on Jan. 18, 2024, 2 pages.
CA Office Action in Canadian Appln. No. 3,099,121, mailed on Dec. 27, 2023, 4 pages.
CN Office Action in Chinese Appln. No. 201980031186.8, mailed on Oct. 21, 2023, 13 pages (with English translation).

* cited by examiner

```
Peltier Plates: 4°C
Flask A: Cultured
Flask B: Culturing
Culture A Phase: Plateau
Cell Count: 4.7xE8/ml
Cell media (A): Added
Cell media (B): Standby
1ml Subtilisin: Added
Incubation: Complete
Filtration: Complete
MitoCount: 9.4 mil/ml
Centrifuge: Complete
```

Fig. 9

AUTOMATED ISOLATION OF VIABLE MITOCHONDRIA

CROSS REFERENCE TO RELATED APPLICATIONS

The present application is the national stage entry of International Patent Application No. PCT/US2019/031312, filed on May 8, 2019, which claims priority to U.S. Provisional Application No. 62/668,358, filed on May 8, 2018, the disclosures of both which are incorporated here by reference in their entirety.

STATEMENT OF FEDERALLY SPONSORED RESEARCH

This invention was made with government support under Grant Number HL103642, awarded by the National Institutes of Health. The Government has certain rights in the invention.

BACKGROUND

Mitochondria exist in every cell in the body except red blood cells and are involved in a large number of important cellular and metabolic processes. Because of these many functions, mitochondrial damage can have detrimental effects. To treat adverse effects in a patient resulting from mitochondrial damage, healthy mitochondria can be isolated from the patient's tissue and transplanted back to the patient at the site of the mitochondrial damage. Mitochondrial isolation can involve processes such as tissue homogenization and differential centrifugation.

SUMMARY

The present disclosure is based, at least in part, on the discovery that viable mitochondria can be isolated from tissue or from cultured cells in a fully automated process. Under computer control, a solution of homogenized tissue or cultured cells are incubated at low temperature for a period of time and then automatically transferred to a filtration station. At the filtration station, a series of filters within increasingly smaller pores are used to filter the incubated solution, thereby removing large organelles and debris from the solution. The filtrate is analyzed by computer-controlled Raman spectrometry to quantify the number of viable mitochondria in the filtrate. When the number of viable mitochondria satisfies a criterion (e.g., the number of viable mitochondria in solution is stable, indicating that filtration of the incubated solution is complete), the filtrate is automatically transferred to a centrifuge that is operated automatically under computer control to separate the viable mitochondria from a supernatant. Following centrifugation, a user can resuspend the viable mitochondria in a clean solution for transplantation into a patient.

In an aspect, an automated isolation device for isolation of viable mitochondria from a solution includes a processor. The automated isolation device includes an incubation station including a holder for a solution containing viable mitochondria; and a cooling system for cooling the holder, the cooling system being controlled by the processor. The automated isolation device includes a first transfer system for transferring solution from the holder of the incubation station to a filtration station, the first transfer system being controlled by the processor. The automated isolation device includes the filtration station, including a series of multiple filters. The automated isolation device includes a spectrometry station including a Raman spectrometer positioned to illuminate a cuvette with light of a first wavelength, the cuvette fluidically coupled to an output of the filtration station, the Raman spectrometer being controlled by the processor; and a detector positioned on a side of the cuvette opposite the Raman spectrometer, the detector being coupled to the processor. The automated isolation device includes a second transfer system for transferring solution from the spectrometry station to a centrifuge, the second transfer system being controlled by the processor. The automated isolation device includes a centrifugation station including the centrifuge, the centrifuge being controlled by the processor, the centrifuge configured to centrifuge the filtrate to separate viable mitochondria from a supernatant.

Embodiments can include one or more of the following features.

The cooling system includes a thermoelectric Peltier refrigeration cooling system controlled by the processor. The Peltier refrigeration cooling system includes a Peltier plate coupled to the processor by an analog-to-digital converter. The Peltier refrigeration cooling system includes a heat dissipation device.

The first transfer system includes a first fluid flow pathway fluidically connecting the holder of the incubation station to the filtration station; and a pump for pumping solution through the first fluid flow pathway, the pump being controlled by the processor. The first fluid flow pathway includes a needle, a first end of the needle aligned with the holder of the incubation station and a second end of the needle connected to tubing that connects to an input to the series of multiple filters. The automated isolation device includes an actuator coupled to the needle, the actuator being controlled by the processor. Actuation of the actuator causes the needle to advance toward the holder of the incubation station.

Each successive filter in the series of multiple filters has a pore size smaller than the previous filter.

A first filter of the series of multiple filters has a pore size of between 30 µm and 50 µm. A second filter of the series of multiple filters has a pore size of between 20 µm and 40 µm. A third filter of the series of multiple filters has a pore size of between 10 µm and 30 µm. A fourth filter of the series of multiple filters has a pore size of between 1 µm and 10 µm.

The filtration station includes a filter cooling system for cooling the series of multiple filters. The filter cooling system includes a thermoelectric Peltier refrigeration cooling system.

The filtration station includes a reservoir fluidically coupled to an output of the series of multiple filters, an output of the reservoir being fluidically coupled to the cuvette.

The spectrometry station includes a filter positioned between the Raman spectrometer and the cuvette.

The automated isolation device includes a bio-incubator in which a cell culture can be cultured. The bio-incubator includes a stirrer controlled by the processor. The bio-incubator includes a heating device controlled by the processor. The bio-incubator includes an oxygen canister. The bio-incubator includes a spectrometer. The automated isolation device includes a third transfer system fluidically connecting the bio-incubator to the incubation station. The automated isolation device includes multiple bio-incubators.

The automated isolation device includes an analog-to-digital converter coupling the processor to the cooling system of the incubation station.

The automated isolation device includes a relay channel coupled to the processor, the relay channel having multiple relays, each relay coupled to a corresponding component of the automated isolation device that is controlled by the processor. The automated isolation device includes a non-transitory computer readable storage medium storing instructions for causing the processor to activate or deactivate the relays of the relay channel in a preprogrammed sequence.

The automated isolation device includes a display.

In an aspect, a method for isolating viable mitochondria from a solution includes incubating a solution of viable mitochondria and a protease enzyme in an incubation station of an automated isolation device; automatically transferring the incubated solution to a filtration station of the automated isolation device by a first transfer system controlled by a processor. The method includes filtering the incubated solution through a series of multiple filters in the filtration station to obtain a filtrate containing viable mitochondria in solution; analyzing the filtrate in a spectrometry station of the automated isolation device using a Raman spectrometry unit controlled by the processor to determine a quantitative characterization of the viable mitochondria in the filtrate. The method includes when the quantitative characterization of the viable mitochondria in the filtrate satisfies a criterion, automatically transferring the filtrate to a centrifugation station of the automated isolation device by a second transfer system controlled by the processor. The method includes in the centrifugation station, centrifuging the filtrate in a centrifuge controlled by the processor to separate the viable mitochondria from a supernatant.

Embodiments can include one or more of the following features.

Incubating the solution includes incubating the solution for a preset, computer-controlled period of time; and automatically transferring the incubated solution to the filtration station at the end of the period of time.

Incubating the solution includes cooling the solution with a thermoelectric Peltier refrigeration cooling system controlled by the processor. Cooling the solution includes controlling a current to a Peltier plate of the thermoelectric Peltier refrigeration cooling system by an analog-to-digital converter coupled to the processor. Cooling the solution includes cooling the solution to a temperature of between 1° C. and about 10° C.

Transferring the incubated solution to the filtration station includes pumping the incubated solution through a needle fluidically connected to the filtration station by a pump controlled by the processor. Transferring the incubated solution to the filtration station includes advancing the needle into the incubated solution by an actuator controlled by the processor.

Filtering the incubated solution through the series of multiple filters includes filtering the incubated solution through successive filters each having a smaller pore size than the previous filter.

Filtering the incubated solution includes cooling the filtration station to a temperature of between 1° C. and 10° C. Cooling the filtration station includes cooling the filtration station with a thermoelectric Peltier refrigeration cooling system controlled by the processor.

Analyzing the filtrate includes illuminating the filtrate from a first side of a cuvette with light of a first wavelength emitted from a Raman spectrometer, and detecting light at a second, opposite side of the cuvette. Detecting light includes receiving the light at a photomultiplier tube that generates an electrical current. The generated electrical current is dependent on a wavelength of the detected light. When there are viable mitochondria in the filtrate, the detected wavelength is different from the first wavelength. The method includes determining the quantitative characterization of the viable mitochondria in the filtrate based on the difference between an electrical current generated by the detected wavelength and an electrical current generated by the first wavelength.

Determining the quantitative characterization includes determining a number of viable mitochondria per unit volume. The method includes determining that the quantitative characterization satisfies the criterion, including determining that the number of viable mitochondria per unit volume is stable.

The method includes receiving, into the incubation station, a container holding the solution, the container inserted into the incubation station by a user. The solution contains homogenized tissue including the viable mitochondria, and the protease enzyme.

The method includes receiving the solution into the incubation station from a bio-incubator in the automated isolation device. The solution includes a cell culture grown in the bio-incubator, cells in the cell culture having viable mitochondria therein. The method includes pumping the protease enzyme into the cell culture in the incubation station by a pump controlled by the processor. The method includes culturing a cell culture in the bio-incubator, the bio-incubator being controlled by the processor. Culturing cells in the bio-incubator includes stirring the cell culture in the bio-incubator using a stirrer controlled by the processor. Culturing cells in the bio-incubator includes heating the cell culture in the bio-incubator using a heating device controlled by the processor. The method includes analyzing the cell culture in a spectrometer controlled by the processor. Analyzing the cell culture includes determining a cell population per unit volume in the cell culture. The method includes determining a cell growth curve based on the results of multiple analyses of the cell culture in the spectrometer. The method includes providing the cell culture as the solution for the incubation station of the automated isolation device when the cell growth curve satisfies a growth criterion. The method includes providing the cell culture when the cell growth curve is in a logarithmic growth phase.

The method includes locking a door of the automated isolation device to prevent access to the stations of the automated isolation device prior to beginning the incubation; and unlocking the door of the automated isolation device following the centrifugation.

The method includes displaying information indicative of a status of the automated isolation device on a display.

In an aspect, a non-transitory computer-readable storage medium stores instructions for causing a computing system to initiate an automated isolation process implemented in an automated isolation device for the isolation of viable mitochondria from a solution; control incubation of the solution in an incubation station of the automated isolation device, including controlling a temperature of the incubation station; after an incubation time period has elapsed, control transfer of a preset volume of the solution from the incubation station to a filtration station of the automated isolation device; control a temperature of the filtration station. The instructions cause the computing system to control a Raman spectrometric analysis of a filtrate output from the filtration station, including controlling a Raman spectrometer in a spectrometry station of the automated isolation device to illuminate a cuvette containing the filtrate from a first side of the cuvette with light of a first wavelength; generating a current from light of a second wavelength received at a second, opposite side of the cuvette; and determining a quantitative characterization of the filtrate based on a difference between the generated current and current generated from light of the first wavelength; and determine that the quantitative characterization of the filtrate satisfies a criterion. The instructions cause the computing system to control transfer of a preset volume of the filtrate from the spectrometry station to each of multiple centrifuge tubes in a centrifuge station of the automated isolation device; and control operation of a centrifuge in the centrifuge station to centrifuge the filtrate in the centrifuge tubes, including controlling the centrifuge to operate at a preset rotational rate and for a preset period of time, the centrifugation of the filtrate causing the viable mitochondria to separate from a supernatant.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

The approaches to automated isolation of viable mitochondria from tissue or from cultured cells can have one or more of the following advantages. The process is rapid and results in relatively high yields of undamaged, viable mitochondria. The process is fully automated without requiring user interaction once the process has begun, thereby freeing human resources for other clinical duties and reducing the possibility of human error. Automated isolation of mitochondria from cultured cells offers the further advantage that viable mitochondria can be obtained without requiring a tissue biopsy from a patient, thus enabling mitochondrial transplantation into patients in emergency situations or patients from whom a biopsy would be damaging or dangerous.

Other features and advantages of the invention will be apparent from the following detailed description and figures, and from the claims.

DESCRIPTION OF DRAWINGS

FIG. 9 is an example of a display.

DETAILED DESCRIPTION

Figure 1:
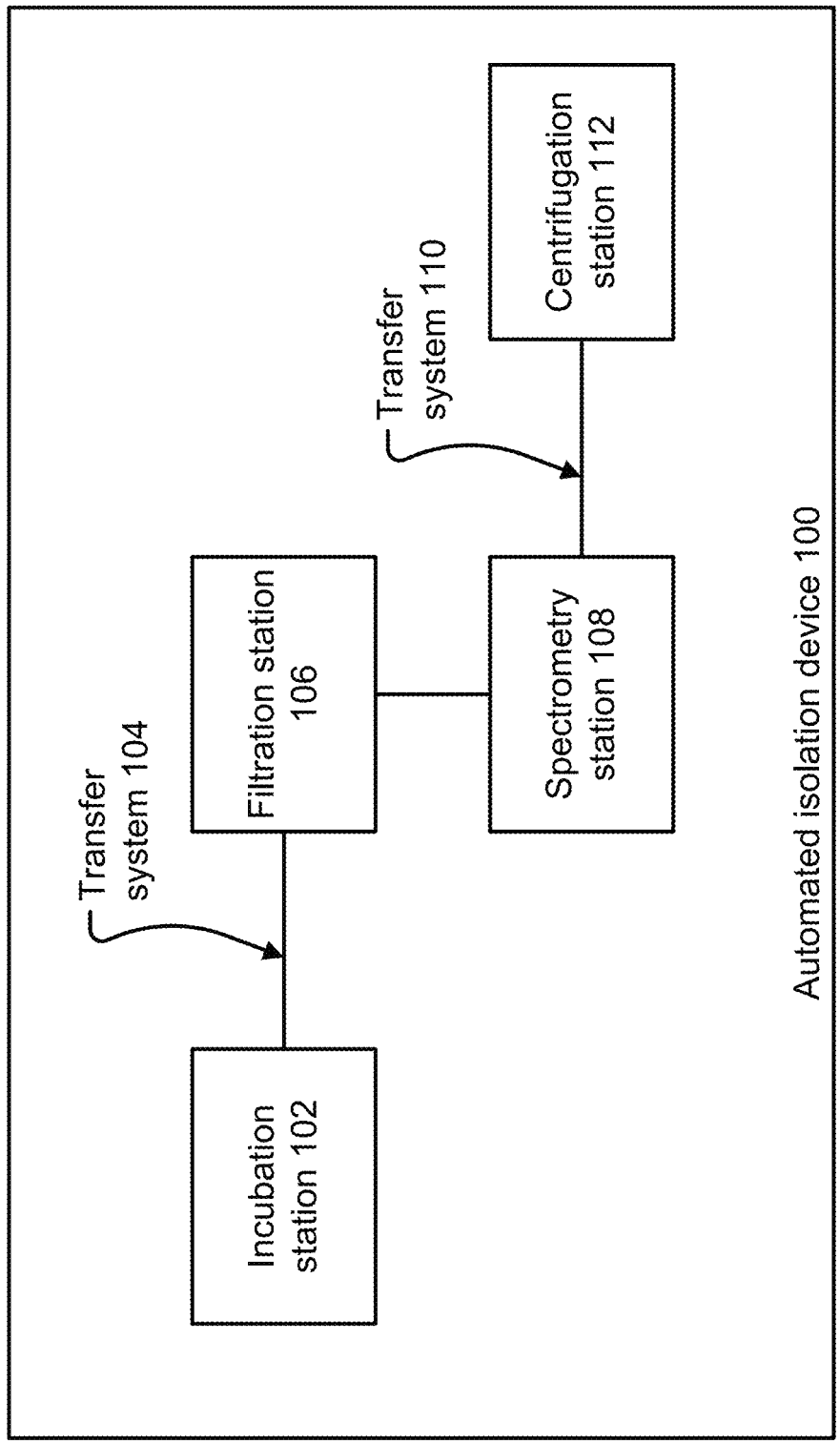
FIG. 1 is a block diagram of an automated isolation device for isolation of viable mitochondria from tissue.

Referring to FIG. 1, in an automated isolation device 100 for isolation of viable mitochondria from tissue, a solution of homogenized tissue, such as homogenized muscle tissue, is incubated in an incubation station 102 at low temperature. In some examples, the solution can be incubated in the presence of an additive such as an enzyme, e.g., a protease. For instance, the enzyme can be Subtilisin A, which is a non-specific protease that cleaves the endoplasmic reticula from cells. Incubation allows larger, undesired cell debris to fall to the bottom of the solution, leaving the viable mitochondria suspended in solution.

After incubation, the solution is transferred by a transfer system 104 including an automated pump to a filtration station 106, where the solution is filtered through a series of filters, each successive filter having a smaller pore size than the previous filter. During the filtration process, larger, undesirable organelles (e.g., cell walls, cell membranes, nuclei, ribosomes, endoplasmic reticula, or other large organelles or debris) are gradually filtered out of solution, leaving a filtrate that is a highly purified solution of viable mitochondria. In some examples, a spectrometry station 108, e.g., a Raman spectrometer, can analyze the filtrate to obtain a quantitative characterization of the mitochondria in solution, such as a number of viable mitochondria in the solution.

The solution of purified mitochondria is transferred by a transfer system 110 including an automated pump to a centrifugation station 112 for isolation of the purified mitochondria from the solution. When the centrifugation is complete, the purified mitochondria can be recovered, resuspended in fresh solution, and transplanted into a patient, e.g., into tissue suffering from mitochondrial damage, such as cardiac or lung tissue.

Figure 2:
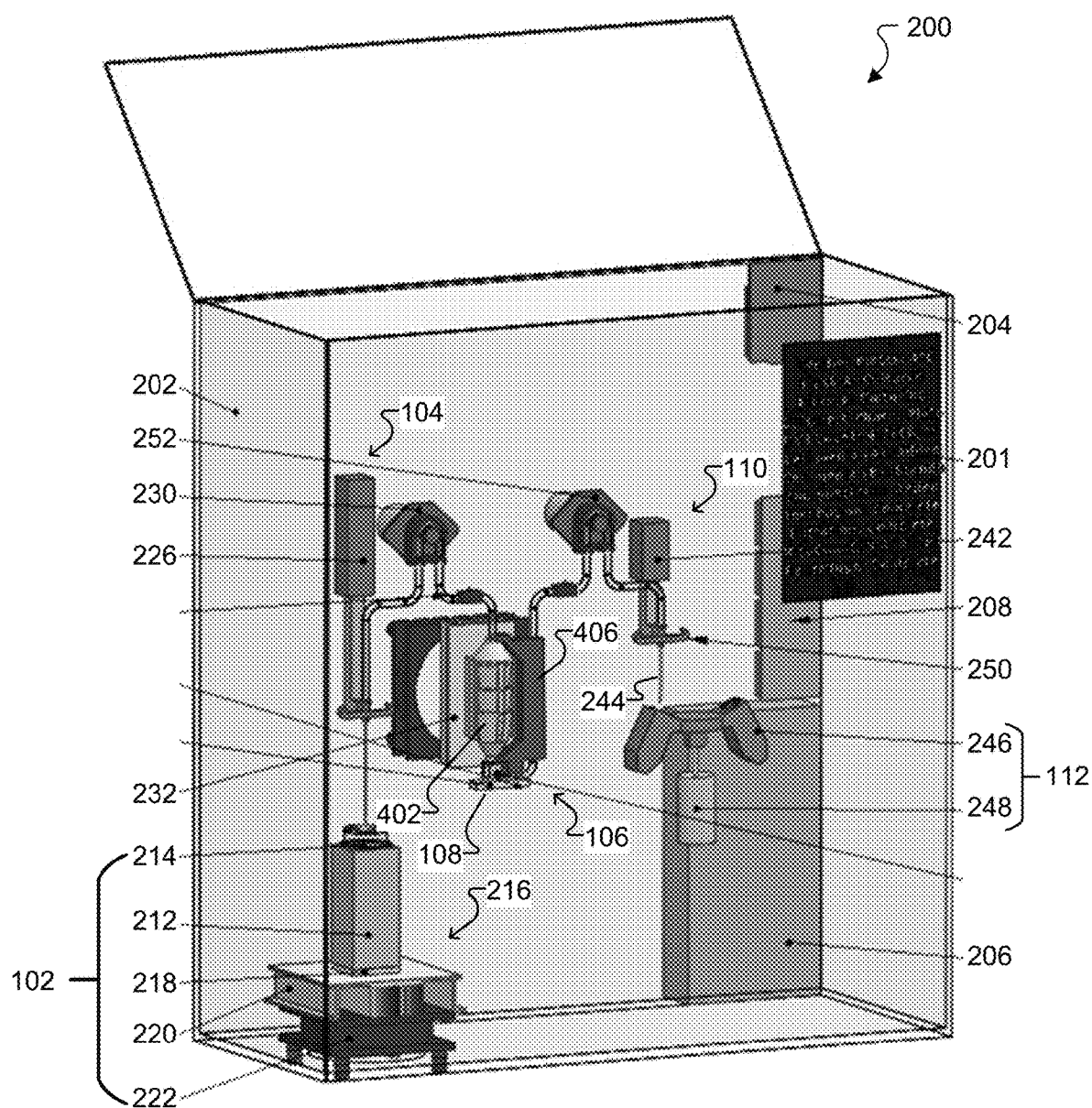
FIG. 2 is a diagram of an automated isolation device.

FIG. 2 shows an example of an automated isolation device 200 for the automated isolation of viable mitochondria from a tissue sample. The automated isolation device 200 is contained within a frame 202, which can be sized to fit on a tabletop. The automated isolation device 200 is designed to operate with minimal user interaction, thereby freeing clinician resources to attend to other patient treatment duties and reducing the risk of human error. For instance, user activities can include turning on the automated isolation device 200, placing disposable components (e.g., an incubation container, a filter unit, and one or more centrifuge tubes) and a tissue sample, activating the automated isolation process, and retrieving the purified viable mitochondria following completion of the process.

The execution of the automated isolation process itself, including the transfer of the mitochondria solution from one station to the next, is an automated process run under computer control. In the example of FIG. 2, a microprocessor 204 that is part of the automated isolation device 200 (e.g., contained within the frame 202 or mounted on the frame 202) controls the operation of the automated isolation device 200. In some examples, the automated isolation device 200 can be connected via a wired or wireless connection to a remote computing device, such as a laptop or desktop computer or a mobile computing device in the clinical environment or a remote server, and the remote computing device can control the operation of the automated isolation device. As used herein, a "computer controlled" component is a component that is controlled by the microprocessor 204 or by a remote computing device connected to the automated isolation device 200.

A display 201, such as a liquid crystal display (LCD), can display status information indicative of the progress of the automated isolation process. In some examples, status information can be provided in other ways, such as by visual indicators (e.g., one or more lights that blink or light up in a given pattern to communicate status information) or audible indicators (e.g., alarms or spoken words to communicate status information). In some examples, when the automated isolation device is connected to a remote computing device, status information can be displayed on a display of the remote computing device. We sometimes refer to the display of information on the display 201; this is to be understood as encompassing display of information on the display 201 of the automated isolation device or on a display of a remote computing device, or as communication of information via visual or audible indicators.

The automated isolation device 200 includes the incubation station 102 in which a solution of homogenized tissue is incubated for a preset, computer-controlled amount of time and at a preset, computer-controlled temperature. The incubation station 102 includes an incubation holder 212 that is sized to receive an incubation container 214, such as a disposable dissociation C tube, inserted by a user. The incubation container 214 contains a solution of homogenized tissue and an enzyme, such as a protease, e.g., Subtilisin A.

The incubation temperature is regulated by a computer-controlled cooling system 216. The cooling system 216 can include a cooling device for cooling the incubation holder 212 and a thermal sensor (not shown) that can provide temperature readings, e.g., to be displayed on the display 201. In some examples, the thermal sensor is coupled to the microprocessor 202 or remote computing device to provide closed-loop temperature feedback, thereby enabling real-time control of the cooling device. In the example of FIG. 2, the cooling device is a thermoelectric Peltier refrigeration cooling system. The Peltier cooling system includes a Peltier plate 218 that converts electrical current into heat and cold energy. The Peltier plate 218 emits cold energy from a first side (e.g., the side facing or contacting the incubation holder 212), e.g., to a steel reservoir, and emits heat from a second, opposite side. A heat sink 220 and a fan 222 disposed at the second side of the Peltier plate 218 dissipate heat away from the incubation station 102. The current to the Peltier plate 218, and thus the temperature to which the incubation holder 212 is cooled, can be controlled electronically by an analog-to-digital (AC-DC) converter 206, discussed further below. Other types of cooling systems can also be used.

Figure 3:
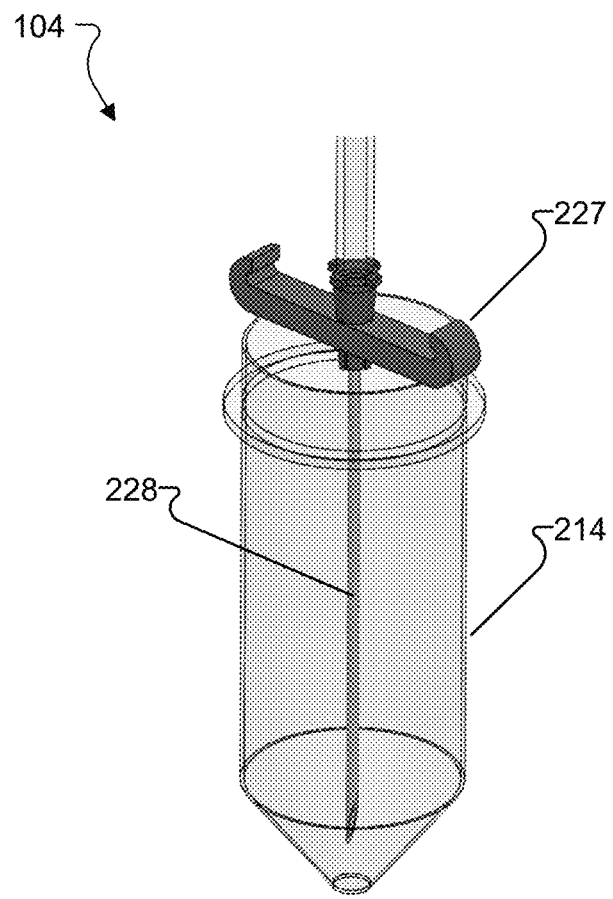
FIG. 3 is a diagram of a portion of a transfer system.

A first computer-controlled transfer system 104 transfers the solution from the incubation container 214 to a filtration station 106 upon completion of the incubation. The first transfer system 104 includes an actuator 226 that, when activated by a signal from the microprocessor 202, advances a needle 228 into the incubation container 214. Referring also to FIG. 3, the actuator 226 can be fitted with a stop mechanism 227, such as a butterfly, that prevents the actuator 226 from advancing the needle 228 all the way to the bottom of the incubation container 214. For instance, the stop mechanism can be positioned to stop the needle about 1 mm from the bottom of the incubation container 214. This prevents the larger, unwanted cell debris that was separated out during the incubation process from being pumped to the filtration station 106, where the larger debris could clog a filter. The first transfer system also includes a computer-controlled pump 230, such as a peristaltic pump, that pumps the incubated solution from the incubation container 214 through delivery tubing to the filtration station 106.

Figure 4:
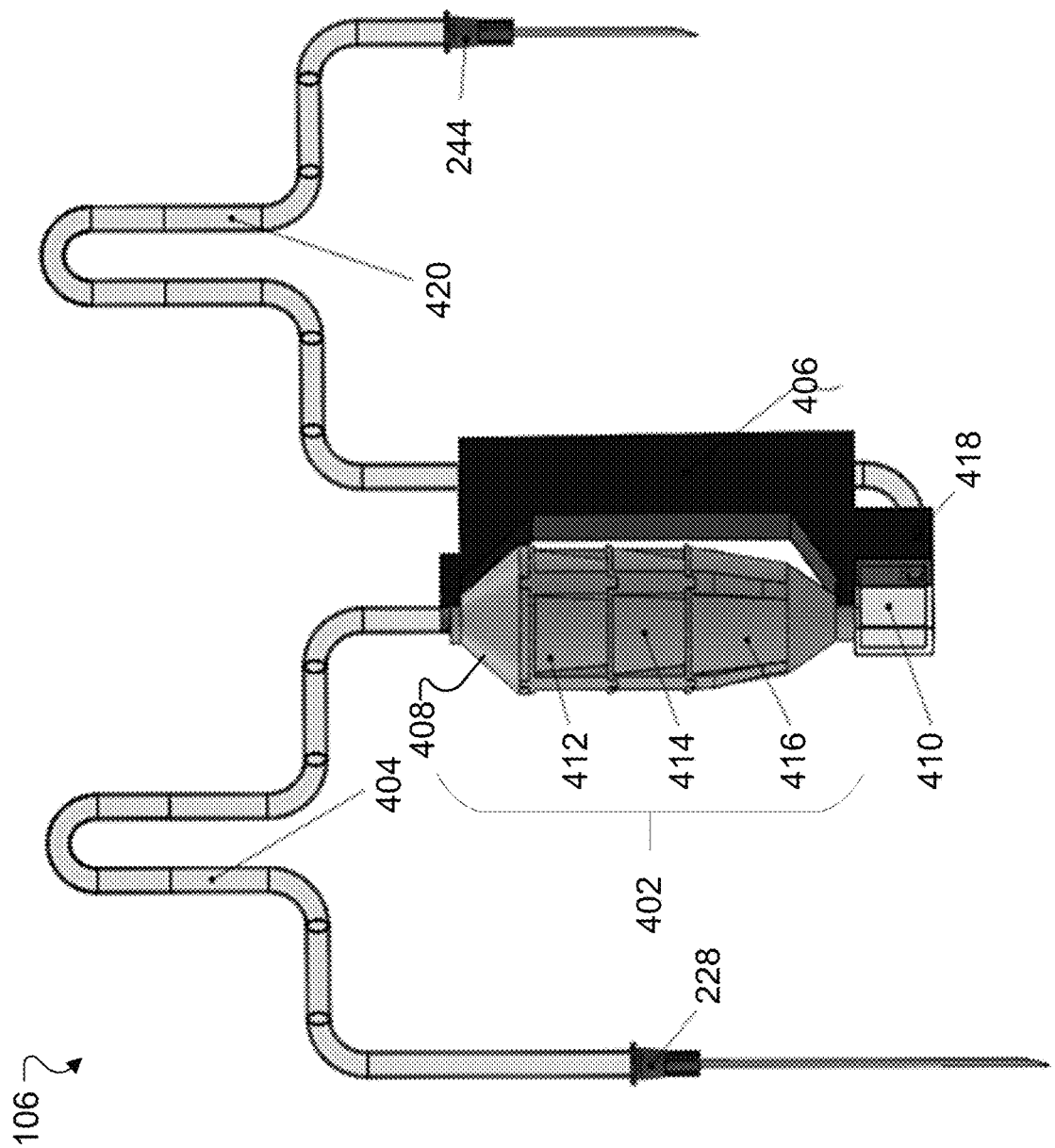
FIG. 4 is a diagram of a filtration station.

Referring FIGS. 2 and 4, incubated solution is provided to the filtration station 106 via an input pathway of the first transfer system 104. The input pathway includes the needle 228 and delivery tubing 404 through which solution is drawn from the incubation container by the pump.

The filtration station 106 includes a disposable filter unit 402 that is cooled by a cooling system 232, such as a Peltier cooling system. The Peltier cooling system 232 includes a Peltier plate that converts electrical current into heat and cold energy. The Peltier plate emits cold energy from a first side (e.g., the side facing or contacting the filter unit 402) and emits heat from a second, opposite side. A heat sink and a fan disposed at the second side of the Peltier plate dissipate heat away from the filter unit 402. The current to the Peltier plate, and thus the temperature to which the filter unit 402 is cooled, is controlled electronically by the AC-DC converter 206. For instance, the Peltier plate can cool the filter unit 402 to a target temperature of between about 1° C. and about 10° C., e.g., 1° C., 2° C., 4° C., 6° C., 8° C., or 10° C. The cooling system 232 can also include a thermal sensor (not shown) that can provide temperature readings, e.g., to be displayed on the display 201. In some examples, the thermal sensor is coupled to the microprocessor 202 or the remote computer to provide closed-loop temperature feedback, thereby enabling real-time control of the Peltier plate. Other types of cooling systems can also be used.

The disposable filter unit 402 is a multi-stage filter system, such as a four-stage filter system, held in place by a filter unit holder 406, e.g., by a connection to cylindrical end portions of the filter unit 402. The filter unit 402 has a top portion 408, such as a tapered (e.g., conical) top portion, with a narrow lumen to which the delivery tubing 404 is attached. The filter unit can have a cross-section that is roughly circular or another shape, such as oval, square, rectangular, triangular, or another shape. The filter unit can be constructed of a biocompatible material, such as polypropylene or polystyrene. In some examples, the filter unit is disposable and is constructed of relatively inexpensive materials to keep down supply costs for the automated isolation device.

A lumen extending through the interior of the filter unit 402 is coupled to the delivery tubing 404. Solution received into the filter unit 402 from the delivery tubing will travel through the lumen to be filtered by each of multiple successive filters, and will exit the filter unit 402 into a collection reservoir 410 coupled to the bottom end of the lumen. Multiple filters 412-416, such as two, three, four, five, or more than five filters, are disposed in series and secured within the lumen of the filter unit 402 such that solution traveling through the lumen is filtered by each of the multiple filters. Each filter can be placed within the lumen of the filter unit 402 at a distance apart from the adjacent filter of at least or about 0.5 mm, e.g., at least or about 1 mm, 2 mm, 3 mm, 4 mm, 5 mm, 8 mm, 1 cm, 2 cm, or 5 cm, or can be in contact with the adjacent filter. In some examples, the spacing between each pair of adjacent filters is uniform; in some examples, the spacing can be different for one or more of the pairs of adjacent filters. The filters can be secured in the lumen of the filter unit using adhesive, a pressure-fit, or by configuring the walls of the lumen in a way that causes the filters to be retained in the lumen (e.g., by designing the lumen walls to have retentive elements such as ridges or grooves).

Each successive filter has a smaller pore size than the previous filter, thus gradually filtering larger, undesirable organelles (e.g., cell walls, cell membranes, nuclei, ribosomes, endoplasmic reticula, or other large organelles or debris) from the solution. After multiple successive filtrations, the resulting filtrate is a highly purified solution of viable mitochondria that exits the filter unit 402 into the collection reservoir 410. The filter unit 402, including each of the multiple filters 412-416, can be sterile.

In an example, the first filter 412 has a pore size of between about 30 μm and about 50 μm, e.g., about 30 μm, about 35 μm, about 40 μm, about 45 μm, or about 50 μm. The second filter 414 disposed within the lumen of the filter unit 402 adjacent to and below the first filter 412, has a pore size of between about 20 µm and about 40 µm, e.g., about 20 µm, about 25 µm, about 30 µm, about 35 µm, or about 40 µm. The third filter 416 disposed within the lumen of the filter unit 402 adjacent to and below the second filter 414, has a pore size of between about 10 µm and about 30 µm, e.g., about 10 µm, about 15 µm, about 20 µm, about 25 µm, or about 30 µm. A fourth filter (not shown) disposed within the lumen of the filter unit 402 adjacent to and below the third filter 416, has a pore size of between about 1 µm and about 10 µm, e.g., about 1 µm, about 2 µm, about 4 µm, about 6 µm, about 8 µm, or about 10 µm. The filters can have a substantially downward conical shape with a superior opening that removes the occurrence of a vacuum during the filtration process. The filters can be formed of any of a variety of filter materials, including, for instance, nylon, mylar, stainless steel, wire mesh, aluminum, synthetic mesh, spectra, Kevlar, plastic, paper, or any combination thereof. Each filter can accommodate between about 1 mL and about 10 mL of solution, e.g., about 1 mL, about 5 mL, or about 10 mL. Further description of filter units can be found in U.S. Patent Publication US 2017/0120237, filed on Dec. 13, 2016, the contents of which are incorporated here by reference in their entirety.

The collection reservoir 410 can have an opening that fluidically connects the collection reservoir 410 to a spectroscopy cuvette 418, such as a cuvette for Raman spectrometry. For instance, the cuvette 418 can have a narrow lumen with openings at both ends. The first opening is fluidically connected to the collection reservoir, and the second opening is fixed to delivery tubing 420.

Figure 5:
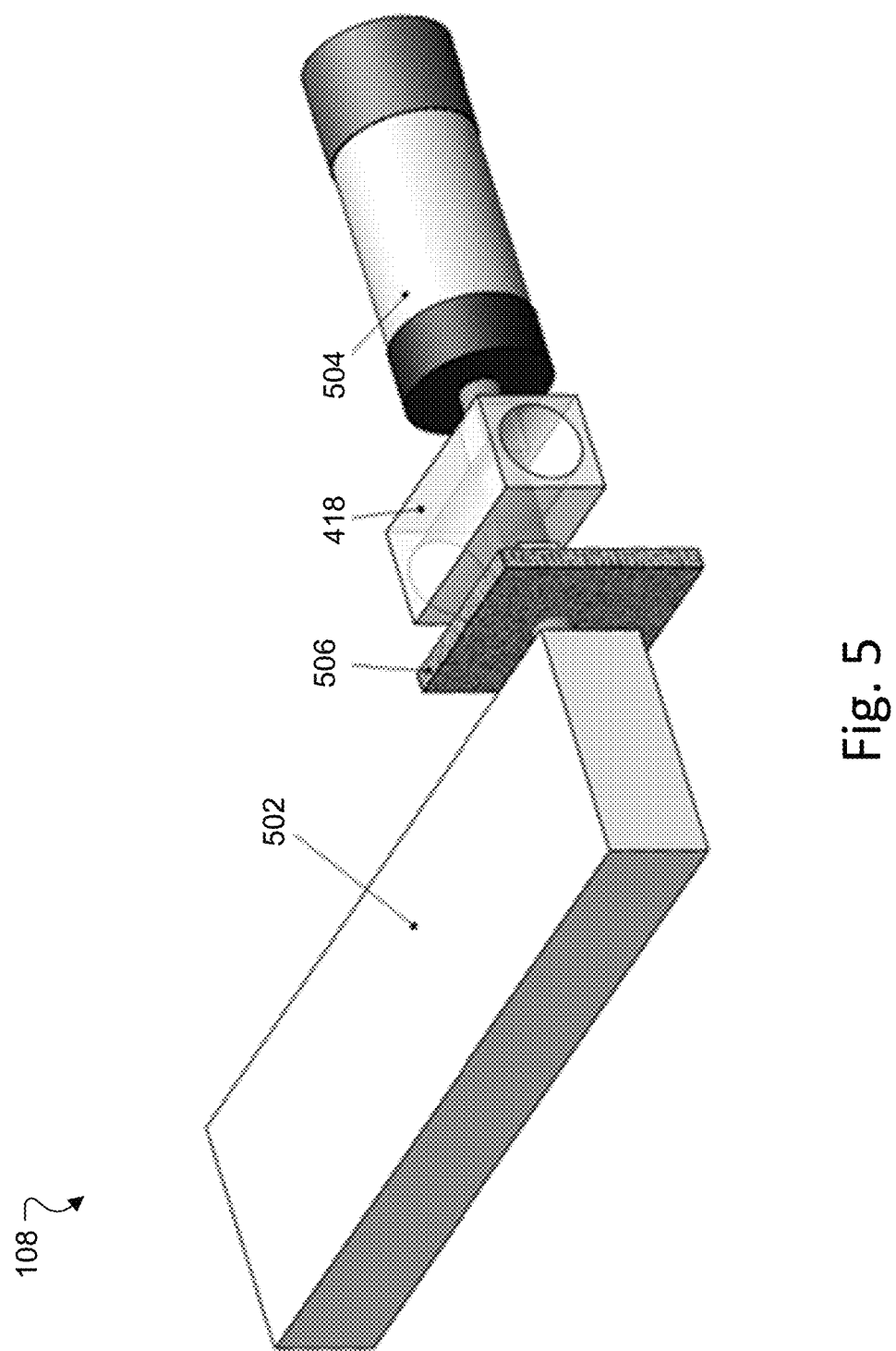
FIG. 5 is a diagram of a spectrometry station.

Referring now to FIGS. 2 and 5, Raman spectrometry in a computer-controlled spectrometry station 108, such as a Raman spectrometry unit, is used to quantify the viability of mitochondria in the filtrate in the cuvette 418. The viability of mitochondria is determined by the presence of the last enzyme, Cytochrome C, on the respiratory electron transport chain; non-viable mitochondria do not possess Cytochrome C. Cytochrome C is a large transmembrane protein complex that Raman scatters photons having wavelengths of about 600-800 $cm^{-1}$, just below the infrared range. The presence of Cytochrome C, and thus the presence of viable mitochondria, can be detected and quantified by illuminating the filtrate with light in this wavelength range, measuring the amount of light that is transmitted through the filtrate, and comparing to the amount of light that is transmitted through a filtrate without Cytochrome C.

The spectrometry station 108 includes a Raman spectrometer 502 that emits a wavelength between about 600 $cm^{-1}$ and about 800 $cm^{-1}$ (e.g., a wavelength of 600 $cm^{-1}$, 650 $cm^{-1}$, 700 $cm^{-1}$, 750 $cm^{-1}$, or 800 $cm^{-1}$). The emitted photons from the spectrometer that are transmitted through the filtered solution in the spectroscopy cuvette 418 are acquired by a photomultiplier tube (PMT) 504, in which photons are converted into an electrical current. In particular, a photocathode in the PMT 504 absorbs the received photons and releases electrons, which are multiplied by a chain of electrodes in the PMT. At the end of this chain, the current flowing from anode to ground is directly proportional to the photoelectron flux generated by the photocathode. In some examples, another detection device can be used instead of the PMT 504, such as a charge-coupled device (CCD) tube.

When Raman spectroscopy is performed on filtrate that contains no Cytochrome C, the photons emitted from the spectrometer 502 are transmitted through the cuvette 418 and impinge on the PMT 504, which generates a current (referred to as the "baseline current") based on the wavelength of the incident light (referred to as the "baseline wavelength"). When the filtrate in the spectroscopy cuvette 418 contains viable mitochondria (and thus contains Cytochrome C), some of the photons emitted from the spectrometer 502 are Raman scattered by the Cytochrome C, causing photons of a second, different wavelength (referred to as the "Raman shifted wavelength) to arrive at the PMT 504. Impingement of light of the Raman shifted wavelength on the PMT 504 causes the PMT 504 to generate a level of current (referred to as the "new current") that is lower than the baseline current. The difference between the baseline current and the new current is directly proportional to the amount of Cytochrome C, and thus the number of viable mitochondria, in the filtrate. The number of viable mitochondria can be calculated using the spectrometry results. In some examples, a filter 506, such as a notch filter or an edge filter, is placed between the spectrometer 502 and the cuvette 418 to block any Raman scattering by the spectrometer 502, which could influence the effect of Cytochrome C on the electron transport chain, thus affecting the accuracy of the results.

As the filtrate accumulates, the wavelength detected by the PMT changes. Once the detected wavelength stabilizes, the microcontroller will use the difference between the baseline standard current and the new current to determine the number of viable mitochondria in a given volume of solution. For instance, a specific algorithm can be used to determine the number of viable mitochondria. The determined number of viable mitochondria can be displayed on the display 201.

Referring again to FIGS. 2 and 4, a second computer-controlled transfer system 110 transfers the solution from the cuvette 418 of the spectrometry station 108 to a centrifugation station 112. The second transfer system includes an actuator 242 that, when activated by a signal from the microprocessor 202, advances a needle 244 into a centrifuge tube 246 (e.g., an Eppendorf tube, e.g., a 2.5 mL Eppendorf tube) held in a rotor of a centrifuge 248. The actuator 242 can have a stop mechanism 250, such as a butterfly, that prevents the actuator from extending too far into the centrifuge tube 246. The second transfer system also includes a computer-controlled pump 252, such as a peristaltic pump, that pumps the filtered solution from the cuvette 418 through the delivery tubing 420 and into the centrifuge tube 246. In the example of FIG. 2, the centrifuge 248 holds two centrifuge tubes 246, and the actuator can be moved relative to the centrifuge 248 so as to transfer solution into each of the centrifuge tubes 246. In some examples, the centrifuge 248 can hold a single centrifuge tube; in some examples, the centrifuge 248 can hold multiple centrifuge tubes, such as 2, 4, 6, 8, 10, or more than 10 tubes.

The centrifuge 248 includes a computer-controlled motor capable of rotating at a rate sufficient to separate the viable mitochondria from the solution. For instance, the motor can rotate at a rate of between about 5,000 revolutions per minute (RPM) and about 15,000 RPM, e.g., 5,000 RPM, 10,000 RPM, or 15,000 RPM. Following centrifugation, a pellet of viable mitochondria remains at the bottom of each centrifuge tube 246.

To control the operation of the automated isolation device 200, the microprocessor 204 or remote computing device communicates electronically with the relay channel 208. Electric power is supplied to the relay 208 by the AC-DC converter 206. Each relay on the relay channel 208 controls the operation of one of the components of the automated isolation device 200, including the display 201; the pumps 230, 252; the actuators 226, 242; the centrifuge motor 254; the Raman spectrometer 502; and the PMT 504. The microprocessor 204 or remote computing device activates and deactivates each relay in a preprogrammed sequence that specifies the sequence in which each relay is to be activated and deactivated and the duration for which each relay is to remain activated. For instance, the preprogrammed sequence can be stored in memory, such as in a non-transitory computer-readable medium, in the automated isolation device 200 or at a remote computing device. The incubation station and the filtration station are not activated by the microcontroller 204 or remote computing device, but rather are powered directly by the AC-DC converter 206 to enable the low temperature of these stations to be maintained.

Figure 6:
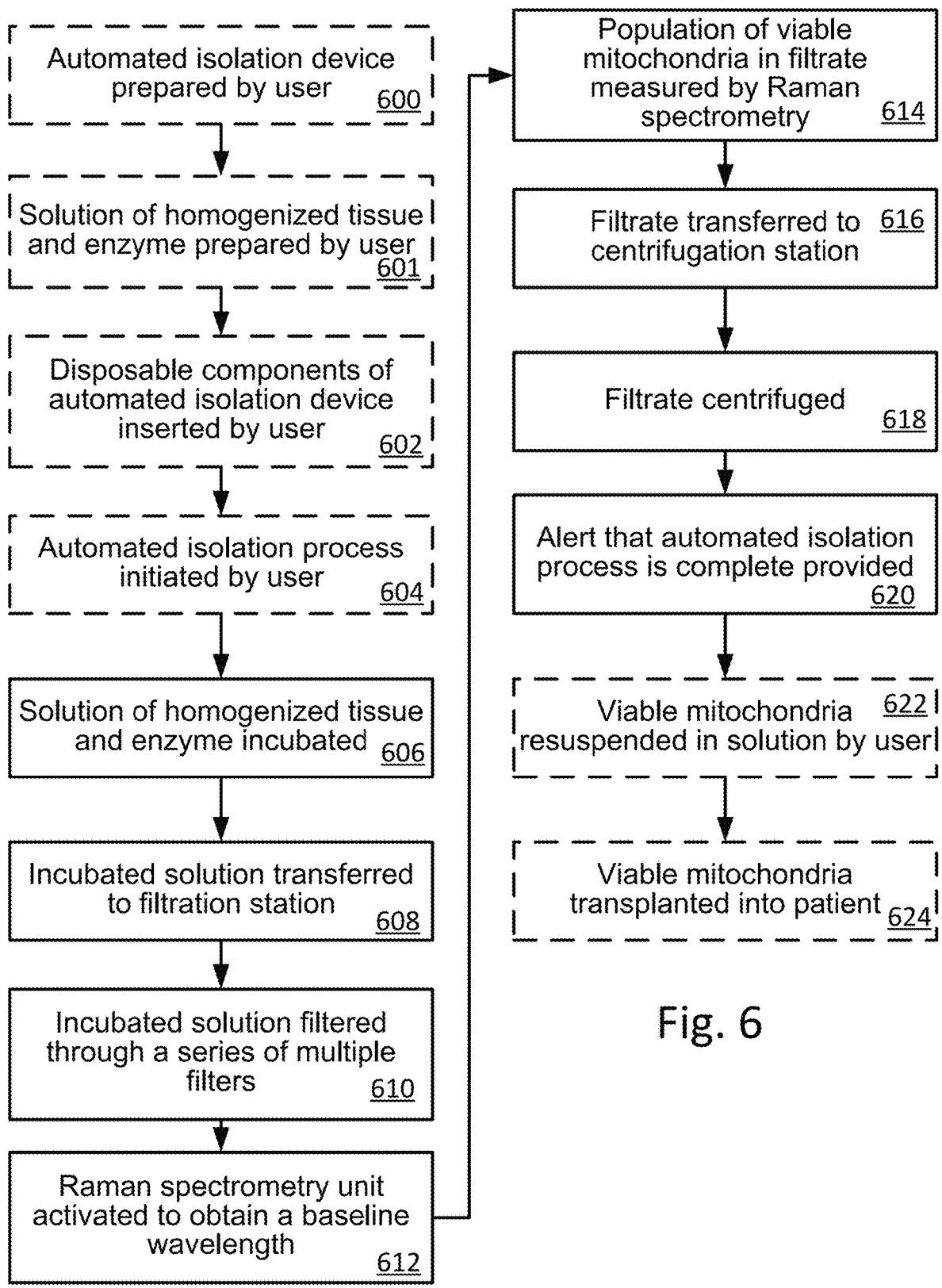
FIG. 6 is a flow chart of a process for operation of an automated isolation device.

FIG. 6 shows an example process for operation of the automated isolation device 200 of FIG. 2. In FIG. 6, actions carried out by a user are shown in dashed lines and actions carried out under automated, computer control are shown in solid lines.

A user prepares the automated isolation device for use (600). The preparation can include turning on (e.g., by plugging in) the automated isolation device in advance of operation, e.g., about 5 minutes, 10 minutes, 15 minutes, 20 minutes, 30 minutes, or another amount of time in advance. Turning the automated isolation device on in advance of operation provides enough time for both the incubation station and the filtration station to turn on and reach their target temperatures before the isolation process begins. In some examples, the display can display the temperatures of the isolation station and the filtration station. When the target temperatures are reached, the display can display an alert, e.g., a ready message or signal or instructions to the user to continuation preparation.

The solution of homogenized tissue and enzyme can be prepared (601) before turning on the automated isolation device or once the device is ready. In a specific example, a tissue sample can be a 6 mm biopsy sample of human muscle tissue. The tissue sample is homogenized in a homogenizing buffer, e.g., Solution A, which is a solution of pH 7.2 containing (e.g., consisting of) 300 mM sucrose, 10 mM K-HEPES (4-(2-hydroxyethyl)-1-piperazineethane-sulfonic acid); pH adjusted with potassium hydroxide) and 1 mM K-EGTA ((ethylene glycol-bis(β-aminoethyl ether)-N,N,N',N'-tetraacetic acid; pH adjusted with potassium hydroxide)

A solution of the homogenized tissue sample and an additive such as an enzyme, such as a protease, e.g., Subtilisin A, is prepared and added to an incubation container (e.g., a dissociation C tube). For instance, the solution can be composed of 5 mL of homogenized tissue in Solution A and 1 mL of Subtilisin A. In some examples, the additive is not used.

Once the automated isolation device is ready, the user inserts the disposable components of the device (602), including (with reference to FIG. 2) the incubation container 214 holding the homogenized solution of tissue and enzyme, the filter unit 402, and the centrifuge tubes 246 (e.g., Eppendorf tubes). In some examples, the display can display the status of the disposable components, e.g., displaying an indication of whether the components are present, not present, or incorrectly placed. In some examples, still with reference to FIG. 2, to insert the disposable filter unit 402 into the automated isolation device, the user uses a handle of the filter unit to snap the filter unit onto the filter unit holder 406 of the filtration station 106 of the automated isolation device. In addition, the user removes safety caps from the needles 228, 244 and inserts each needle into its corresponding stop mechanism 227, 250, and attaches delivery tubing 404, 420 to each pump 230, 252.

After all of the disposable components are inserted, the user closes the door of the automated isolation device and starts the isolation process (604), e.g., by pressing a switch or button, by interacting with the display, by starting the process from a remote computing device connected to the automated isolation device, or in another way. In some examples, the display can display a status indicating that the incubation process has begun.

Once the user has initiated the isolation process, the process proceeds under computer control without further user interaction unless the process is completed. In some examples, the door of the automated isolation device remains locked until the process is completed. In some examples, if the door is not properly closed when the user attempts to start the process, an alert can be provided, such as a visible alert (e.g., a light, information on the display) or an audible alert (e.g., an alarm).

In the incubation station, the solution of homogenized tissue and enzyme is incubated (606) for a preset, computer-controlled amount of time at a preset, computer-controlled low temperature (e.g., between about 1° C. and about 10° C., e.g., 1° C., 2° C., 4° C., 6° C., 8° C., or 10° C.) for a period of time (e.g., between about 2 minutes and about 30 minutes, e.g., 2 minutes, 5 minutes, 10 minutes, 15 minutes, 20 minutes, 25 minutes, 30 minutes, or another amount of time), which allows the larger, undesired cell debris to fall to the bottom of the solution, leaving the viable mitochondria suspended in solution. When the preset incubation time has elapsed, the display can display a status indicating that the incubation process is complete.

Following incubation, the first transfer system is activated to transfer the incubated solution from the incubation container to the filtration station (608). The computer activates the actuator of the first transfer system, which draws the needle into the incubation container. When the needle reaches the target distance (e.g., as controlled by the computer, or when the needle advance is stopped by the stop mechanism), the computer deactivates the actuator, which remains in an extended position. The computer then activates the pump for a preset amount of time (e.g., between about 1 second and about 30 seconds, e.g., 1 second, 2 seconds, 5 seconds, 10 seconds, 15 seconds, 20 seconds, 25 seconds, 30 seconds, or another amount of time) to pump the incubated solution from the incubation container to the filtration station. The preset amount of time can be sufficient to pump a set volume of solution, e.g., between about 1 mL and about 10 mL, e.g., 1 mL, 2 mL, 5 mL, 10 mL, or another amount of solution. When the pumping time has elapsed, the computer turns off the pump and activates the actuator to retract the needle. The display can display a status indicating that the filtration process has begun.

The incubated solution is filtered at the filtration station (610) by passing sequentially through each of a series of multiple (e.g., two, three, four, or five) filters of the filter unit. Each successive filter has a smaller pore size than the previous filter, thus gradually filtering larger, undesirable organelles (e.g., cell walls, cell membranes, nuclei, ribosomes, endoplasmic reticula, or other large organelles or debris) from the solution. The solution progresses through the series of filters, e.g., by force of gravity or by capillary action. After multiple successive filtrations, the resulting filtrate is a highly purified solution of viable mitochondria that exits the filter unit into the collection reservoir and into the spectroscopy cuvette. Filtration through the series of multiple filters in the filter unit subjects mitochondria to less mechanical stress than would a filtration using standard differentiation centrifugation protocols. The filtration station can be maintained at a computer-controlled low temperature (e.g., between about 1° C. and about 10° C., e.g., 1° C., 2° C., 4° C., 6° C., 8° C., or 10° C.).

The computer activates the Raman spectrometer and the PMT in the Raman unit to obtain a baseline wavelength (612). In some examples, the Raman spectrometer and PMT can be activated substantially concurrently with delivery of the fluid from the incubation container to the filtration station. The spectrometer emits a steady, continuous emission of light of constant wavelength through the Raman filter (if present) and cuvette and toward the PMT. The PMT continuously absorbs a standard, constant wavelength of light and relays this information as electric current back to the microcontroller. This initial wavelength is the baseline wavelength against which the measurement of mitochondrial viability will be based.

As filtrate begins to accumulate in the cuvette following filtration, the population of viable mitochondria in the filtrate is measured by the Raman unit (614). As the filtrate accumulates, the wavelength detected by the PMT changes (i.e., to the Raman shifted wavelength) due to Raman scattering by the Cytochrome C on the viable mitochondria in the filtrate. Once the wavelength detected by the PMT stabilizes (meaning there is no significant change in the detected wavelength between a first point in time and a second point in time), the microcontroller will use the difference between the baseline wavelength and the Raman shifted wavelength to determine the number of viable mitochondria in a given volume of solution. When a consistent count of mitochondria in solution is obtained (meaning there is no significant change in the determined number of viable mitochondria between a first point in time and a second point in time), the filtration process is complete and the computer turns off the spectrometer and PMT. In some examples, the display can display a status indicating that the filtration process is complete. In some examples, the display can display the calculated number of mitochondria per volume.

Following filtration, the second transfer system is activated to transfer the incubated solution from the cuvette to the centrifugation station (616). The computer activates the actuator of the transfer system, which draws the needle into one of the centrifuge tubes that is aligned with the needle. When the needle reaches the target distance (e.g., as controlled by the computer, or when the needle advance is stopped by the stop mechanism), the computer deactivates the actuator, which remains in an extended position. The computer then activates the pump for a preset amount of time (e.g., between about 1 second and about 15 seconds, e.g., 1 second, 2 seconds, 5 seconds, 10 seconds, 15 seconds, or another amount of time) to pump the filtered solution from the cuvette to the centrifuge tube. The preset amount of time can be sufficient to pump a set volume of solution, e.g., between about 1 mL and about 5 mL, e.g., 1 mL, 2 mL, 2.5 mL, 3 mL, 4 mL, 5 mL, or another amount of solution. When the pumping time has elapsed, the computer turns off the pump and activates the actuator to retract the needle, and activates the centrifuge motor to rotate the centrifuge such that another one of the centrifuge tubes is aligned with the needle. The process is repeated to transfer filtered solution into the next centrifuge. When all centrifuge tubes have received solution, or when no solution remains in the cuvette, the LCD screen can display a status indicating that the filtrate has been transferred.

The filtered solution is centrifuged (618). The computer activates the centrifuge motor to rotate at between about 5,000 revolutions per minute (RPM) and about 15,000 RPM, e.g., 5,000 RPM, 10,000 RPM, or 15,000 RPM; for a preset time, e.g., between about 1 minute and about 15 minutes, e.g., 1 minute, 5 minutes, 10 minutes, 15 minutes, or another amount of time. During the centrifugation process, the display can display the remaining centrifugation time.

Once the centrifugation is completed, the computer turns off the centrifuge motor and an indicator (e.g., a visible indicator (e.g., a light, information on the display screen) or an audible indicator) is provided to alert the user that the isolation process is complete (620). The door is unlocked.

Upon completion of the automated isolation process, the user can remove unwanted supernatant solution from the centrifuge tubes, leaving a pellet of viable mitochondria remaining in each tube that can be resuspended in solution (622), e.g., a homogenizing solution, such as Solution A. The viable mitochondria are then ready for transplantation into a patient (624). To complete the process, the user removes disposable components from the automated isolation device, such as the filter unit, pumps, needles, tubing, and the incubation container.

In some examples, the automated isolation process can be completed relatively rapidly, such as in 30 minutes or less, e.g., 10 minutes, 15 minutes, 20 minutes, 25 minutes, or 30 minutes. The automated isolation process can produce a relatively high yield of viable, respiration-competent mitochondria. For instance, the automated isolation process can yield about $2 \times 10^{10}$ viable mitochondria from 0.18±0.04 g (wet weight) of tissue sample.

Figure 7:
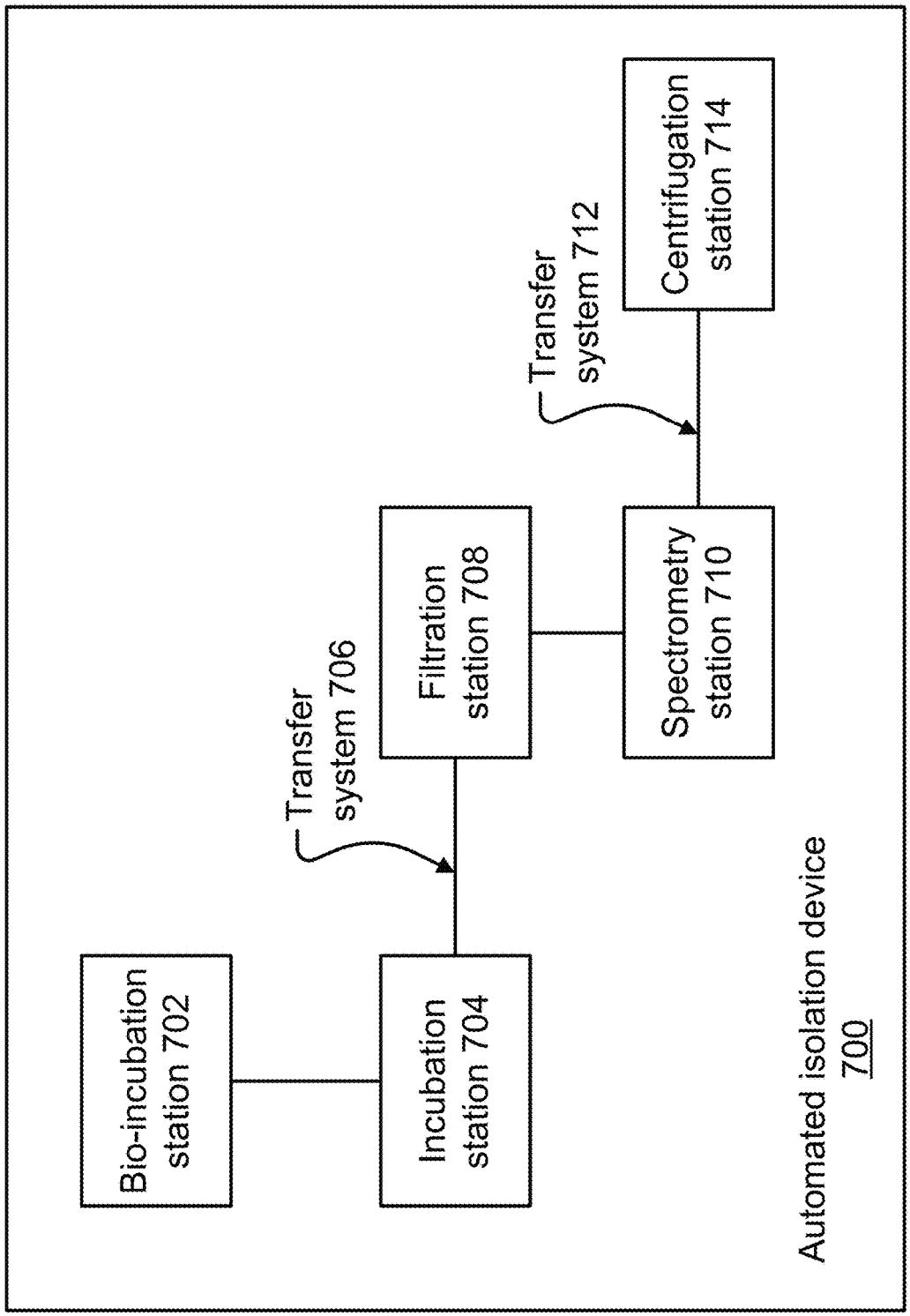
FIG. 7 is a block diagram of an automated isolation device for isolation of viable mitochondria from cultured cells.

Referring to FIG. 7, in an automated isolation device 700 for the automated isolation of viable mitochondria from cultured cells. The automated isolation device 700 enables viable mitochondria to be isolated for transplantation into a patient without first obtaining a tissue sample from the patient. For instance, harvesting viable mitochondria from bio-incubated cells can be useful for treating patients for whom finding a location to obtain a sample of mitochondria-containing tissue can be difficult, such as pediatric patients or patients having hard or ischemic tissue. Harvesting viable mitochondria from bio-incubated cells can also be useful in emergency situations in which there may not be time to obtain and homogenize a tissue sample from a patient, such as in an emergency vehicle or in an emergency ward.

In the automated isolation device 700, cells are cultured in a bio-incubator 702. Responsive to a request for viable mitochondria, cultured cells are pumped from the bio-incubator to an incubation station 704 of the automated isolation device. In the incubation station, the cultured cells are incubated in a solution (e.g., Solution A) at low temperature in the presence of an additive such as an enzyme, e.g., a protease, such as Subtilisin A. Incubation allows larger, undesired cell debris to fall to the bottom of the solution, leaving the viable mitochondria suspended in solution.

After incubation, the solution is transferred by a transfer system 706 including an automated pump to a filtration station 708, where the solution is filtered through a series of filters, each successive filter having a smaller pore size than the previous filter. During the filtration process, larger, undesirable organelles (e.g., cell walls, cell membranes, nuclei, ribosomes, endoplasmic reticula, or other large organelles or debris) are gradually filtered out of solution, leaving a filtrate that is a highly purified solution of viable mitochondria. In some examples, a spectrometry station 710, e.g., a Raman spectrometer, can analyze the filtrate to obtain a quantitative characterization of the mitochondria in solution, such as a number of viable mitochondria in the solution.

The solution of purified mitochondria is transferred by a transfer system 712 including an automated pump to a centrifugation station 714 for isolation of the purified mitochondria from the solution. When the centrifugation is complete, the purified mitochondria can be recovered, resuspended in fresh solution, and transplanted into a patient, e.g., into tissue suffering from mitochondrial damage, such as cardiac tissue.

Figure 8:
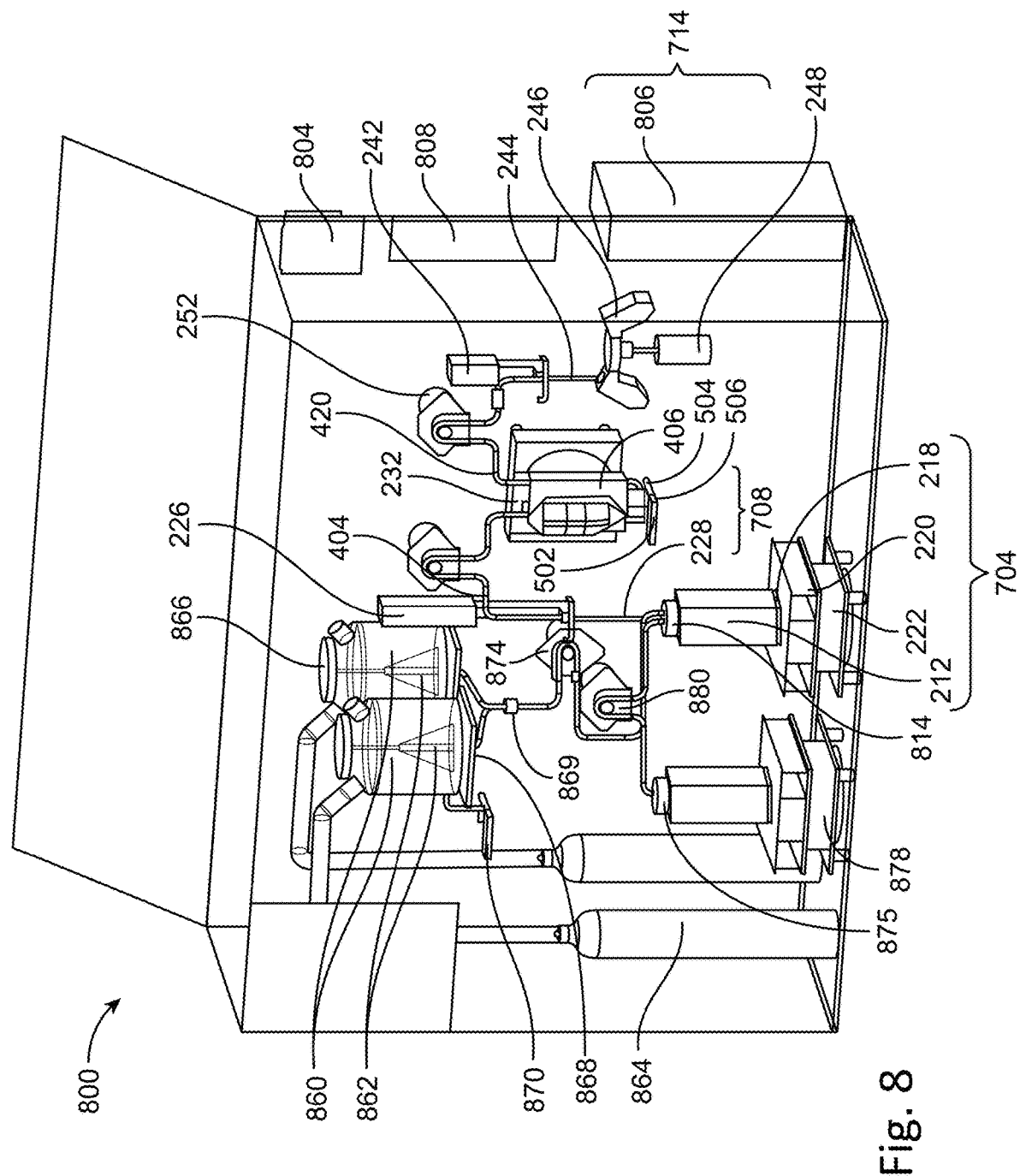
FIG. 8 is a diagram of an automated isolation device.

FIG. 8 shows an example of an automated isolation device 800 for the automated isolation of viable mitochondria from bio-incubated cells. In the automated isolation device 800, cell cultures are grown in bio-incubators and viable mitochondria are isolated from these cultured cells. Patient tissue does not need to be used as an input for the automated isolation device 800.

The automated isolation device 800 is designed to operate with minimal user interaction, and runs under computer control. In the example of FIG. 8, a microprocessor 804 that is part of the automated isolation device 800 controls the operation of the automated isolation device. In some examples, the automated isolation device 800 can be connected via a wired or wireless connection to a remote computing device, such as a laptop or desktop computer in the clinical environment or a remote server, and the remote computing device can control the operation of the automated isolation device. The microprocessor 804 can control the components of the automated isolation device 800 via a relay channel 808 powered by an analog-to-digital converter 806, e.g., that operates similarly to the relay channel 208 described above with respect to FIG. 2. A display 801, such as an LCD, can display status information indicative of the progress of the automated isolation process and of the growth of the cell cultures in the bio-incubators.

The bio-incubation station 702 of the automated isolation device 800 includes one or more bio-incubators 860 in which cells are cultured in preparation for mitochondria isolation. Cells and a cell culture medium can be added to suspension to both bio-incubators 860, e.g., on a schedule (e.g., once per day, twice per day, or with another frequency) or on an as-needed basis, and incubated for growth. The cells can be supplied frozen in a sterile, coded package with media. In some examples, at least two bio-incubators are present to provide for overlapping cell culture, e.g., to allow for one bio-incubator to remain in culture to allow for continuous growth optimization while the other bio-incubator releases cells for mitochondrial isolation. For instance, cells can be released from a bio-incubator when the cell culture is in a logarithmic growth phase of a cell growth curve; in other phases of the cell growth curve, the cells can be maintained in the bio-incubator for further culturing. In some examples, only a single bio-incubator can be used.

Each bio-incubator 860 includes a spinning flask 862 in which the cells are cultured for growth. Each spinning flask is attached to an oxygen canister 864 and is controlled by a stirrer 866, e.g., a hotplate stirrer. The stirrer can control the rotational speed of a spinner 868 while also heating the spinning flask 862 to a temperature conducive to cell culture, e.g., between about 35° C. and about 40° C., e.g., 35° C., 36° C., 37° C., 38° C., 39° C., or 40° C. The stirrer 866 is computer controlled, e.g., via the relay channel 808. In some examples, stirring and heating functionality are provided by two distinct devices.

In some examples, a sample of the cell culture (e.g., a 1 mL sample) can be analyzed by spectrometry to measure the number of cultured cells per unit volume in the sample. For instance, samples can be taken at frequent time intervals, such as once every 15 minutes, once every 30 minutes, once per hour, once every two hours, or at another interval. The spectrometric analysis of cell population can be an automated, computer-controlled process. Each bio-incubator 860 can include a spectrometer 870 and a PMT (not shown). The spectrometer 870 can emit light at a wavelength that is reflected by viable cells in the cell culture. In the absence of viable cells, the PMT absorbs the photons emitted from the spectrometer 870 through a photocathode, which releases electrons that are multiplied by a chain of electrodes. The resulting current is proportional to the photoelectron flux generated by the photocathode. When a sample containing viable cells is placed between the spectrometer 870 and the PMT, the cells reflect some of the photons away from the PMT, and the PMT thus absorbs less light and thus generates a smaller current. The difference in the amount of light absorbed by the PMT, and thus the difference in the generated current, is directly proportional to the number of viable cells in the sample. The number of viable cells can thus be calculated using the spectrometry results. Moreover, a growth curve can be determined based on the time at which each sample is analyzed. The growth curve can be compared to a standardized growth curve to determine cell number and cell purity. In some examples, data, such as cell growth time and cell count per volume, can be displayed on a computer screen that is connected to the automated isolation device 800.

Data obtained by spectrometry, such as cell growth time and cell count data, can be used to determine which bio-incubator 860 (if any) is available to provide cells responsive to a request for isolated viable mitochondria. For instance, a bio-incubator can be available if the cells in that bio-incubator are in a logarithmic growth phase of the growth curve. Once a plateau phase in the growth curve has been reached in which the number of cells per volume is stable, the bio-incubator is made unavailable and cells can be provided from another bio-incubator having cells that are in the growth phase.

A user can request isolated viable mitochondria through a computer interface of a computer connected to the automated isolation device, by pressing a button or switch, by interacting (e.g., tapping on) the LCD screen, or in another way. Responsive to a received request for mitochondria, the computer calculates the target number of cells to be provided in order to obtain the desired number of mitochondria. Each bio-incubator 860 includes a pneumatic valve 869 that connects the bio-incubator to an incubation tube 814 in an incubation station 704. The pneumatic valve 869 for the available bio-incubator is opened under computer control for an amount of time sufficient to transfer the target number of cells to the incubation tube 814. For instance, the cells can be pumped through the pneumatic valve 869 from the bio-incubator 860 to the incubation tube 814 by a pump 874, such as a computer-controlled peristaltic pump.

Incubation additives, such as an enzyme (e.g., Subtilisin A); and solutions (e.g. Solution A) are each stored as a sterile solution in an incubation tube 875 in a reservoir 876. The temperature of the reservoir 876 is regulated by a cooling system 878, such as a thermoelectric Peltier refrigeration cooling system (e.g., a cooling system similar to the cooling system 216 described with respect to FIG. 2). In some examples, the temperature of the incubation tubes can be displayed on the LCD or on a computer display. When cells are pumped into the incubation tube 814, an appropriate volume of additive and solution (e.g., Subtilisin A and Solution A) are pumped from the reservoir 876 to the incubation tube 814 by a pump 880, such as a computer-controlled peristaltic pump. In some examples, the volume of the additive (e.g., Subtilisin A) can be measured by a flow control device, such as a pneumatic flow control valve, that can be controlled computationally by computer.

The components and function of the incubation station 704 are the same as those of the incubation station 102 described above with respect to FIG. 2. For instance, the incubation temperature is regulated by the cooling system 216, such as a computer-controlled thermoelectric Peltier refrigeration cooling system. Incubation of the cells with an additive and solution (e.g., Subtilisin A and Solution A) proceeds as described above with respect to FIG. 2. Incubation allows larger, undesired cell debris to fall to the bottom of the solution, leaving the viable mitochondria suspended in solution.

Following incubation, the solution is transferred from the incubation station 704 to a filtration station 708 by a first transfer system. The components and function of the first transfer system are described above with respect to FIG. 2. The components and function of the filtration station 708 are the same as those of the filtration station 106, described above with respect to FIG. 4. For instance, the filter unit of the filtration station 708 includes multiple filters, each successive filter having a smaller pore size than the previous filter, such that larger, undesirable organelles are gradually removed from solution. After multiple successive filtrations, the resulting filtrate is a highly purified solution of viable mitochondria.

The filtrate can be analyzed by Raman spectrometry in a Raman unit 710 to quantify mitochondrial viability in the filtrate. The components and function of the Raman unit 710 are the same as those of the Raman unit 108 described above with respect to FIG. 5.

A second transfer system transfers the filtrate from the cuvette 418 of the Raman unit 710 to a centrifugation station 714. The components and function of the second transfer system are described above with respect to FIG. 2. The components and function of the centrifugation station 714 are the same as those of the centrifugation station 112 described above with respect to FIG. 2. Following centrifugation, a pellet of viable mitochondria remains at the bottom of each centrifuge tube 246.

Upon completion of the automated isolation process, the user can remove unwanted supernatant solution from the centrifuge tubes, leaving a pellet of viable mitochondria remaining in each tube that can be resuspended in a solution, such as Solution A. The viable mitochondria are then ready for transplantation into a patient. To complete the process, the user removes disposable components from the automated isolation device, such as the filter unit, pumps, needles, tubing, and the incubation container.

FIG. 9 is an example of information shown on the display of the automated isolation device. The display can communication information such as the temperature of the cooling systems (e.g., the Peltier plates) of the incubation station and the filtration station; the status of one or more of the bio-incubators; the growth phase of the cell culture in one or more of the bio-incubators; the cell count in one or more of the bio-incubators; the status of the cell media in one or more of the bio-incubators; the composition of the solution in the incubation station (e.g., whether Subtilisin A has been added); the status of each of one or more phases of the automated isolation process (e.g., incubation, filtration, and centrifugation); and the count of viable mitochondria in the filtrate as determined by Raman spectrometry. Additional information can be display. In some examples, less information than is shown in FIG. 9 can be displayed. In some examples, some or all of this information can be communicated in other ways, such as by lights or audible alerts, or by display on an interface of a remote computing device such as a desktop or laptop computer or a mobile computing device.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An automated isolation device for isolating viable mitochondria from cells cultured in a bio-incubator, the automated isolation device comprising:
   a microprocessor configured to control the operation of the automated isolation device;
   one or more bio-incubators, wherein the bio-incubators are configured to culture cells in preparation for mitochondria isolation;
   a pump configured to transfer the cultured cells from the bio-incubator to an incubation station;
   the incubation station comprising
      a holder for a solution containing viable mitochondria; and
      a cooling system for cooling the holder, the cooling system being controlled by the microprocessor; and
   wherein the incubation station is configured to incubate the cultured cells in the incubation station in a sterile solution at low temperature in the presence of an additive, such as an enzyme;
   a first transfer system including a first automated pump, the first transfer system configured to, after the incubation of the cells, transfer the sterile solution containing the cultured cells from the incubation station to a filtration station;
   the filtration station comprising a series of filters, each successive filter having a smaller pore size than the previous filter;
   a second transfer system including a second automated pump, the second transfer system configured to transfer filtered solution from the filtration station to a centrifugation station, the filtered solution comprising purified mitochondria; and
   the centrifugation station for isolation of the purified mitochondria from the filtered solution.

2. The automated device of claim 1 wherein the bio-incubator comprises at least two bio-incubators.

3. The automated isolation device of claim 1, wherein each bio-incubator comprises a spinning flask in which the cells are culture for growth, wherein each spinning flask is configured to be attached to an oxygen canister, and wherein each spinning flask is controlled by a stirrer.

4. The automated isolation device of claim 1, further comprising a spectrometer configured to analyse each of multiple samples of a cell culture of one or more of the bio-incubators and determine the number of cultured cells per unit volume in each sample, in which multiple samples are taken from each of the one or more bio-incubators at prescribed time intervals.

5. The automated device of claim 4, wherein the pump is configured to transfer the cultured cells responsive to request for viable mitochondria, and in which an operation of the pump responsive to the request is determined based on the determined number of cultured cells per unit volume in a given sample of the cell culture.

6. The automated isolation device of claim 4, wherein the analysis of the sample of the cell culture and the determination of the number of cultured cells per unit volume in the sample is an automated computer-controlled process.

7. The automated device of claim 4, wherein the number of cultured cells per unit volume in the samples taken from a given one of the bio-incubators at each time interval determines the availability of a bio-incubator to provide cultured cells.

8. The automated device of claim 7, wherein the bio-incubator comprises at least two bio-incubators; and wherein a given bio-incubator
   (i) is available to provide cultured cells when the number of cultured cells per unit volume in the samples taken at multiple successive time intervals has a logarithmic growth; and
   (ii) is made unavailable when the number of cultured cells per unit volume in the samples taken at multiple successive time intervals is stable.

9. The automated device of claim 7, wherein
   i) each bio-incubator includes a pneumatic valve that connects the bio-incubator to an incubation tube in the incubation station; and
   ii) the pneumatic valve for the available bio-incubator is configured to be opened under computer control for an amount of time sufficient to transfer a target number of cells to the incubation tube.

10. The automated device of claim 1, wherein the sterile solution is Solution A and the enzyme is Subtilisin.

11. The automated device of claim 1, wherein the filtration station, includes multiple filters, wherein
   i) a first filter of the series of multiple filters has a pore size of between 30 μm and 50 μm;
   ii) a second filter of the series of multiple filters is disposed within the lumen of the filter unit adjacent to and below the first filter and has a pore size of between 20 μm and 40 μm;
   iii) a third filter of the series of multiple filters is disposed within the lumen of the filter unit adjacent to and below the second filter and has a pore size of between 10 μm and 30 μm,
   iv) a fourth filter of the series of multiple filters is disposed within the lumen of the filter unit adjacent to and below the third filter and has a pore size of between 1 μm and 10 μm.

12. The automated device of claim 1, comprising a spectrometry station configured to analyse a filtrate output from the filtration station.

13. The automated device of claim 12, wherein the spectrometry station is a Raman spectrometry station, comprising:
   a Raman spectrometer positioned to illuminate a cuvette with light of a first wavelength, the cuvette fluidically coupled to an output of the filtration station, the Raman spectrometer being controlled by the microprocessor; and
   a detector positioned on a side of the cuvette opposite the Raman spectrometer, the detector being coupled to the microprocessor.

14. The automated device of claim 3, wherein the stirrer is a hotplate stirrer.

15. The automated device of claim 1, wherein each bio-incubator comprises a spectrometer and a photomultiplier tube (PMT) configured to analyze a sample of the cell culture, in which
   i) the spectrometer is configured to emit light at a wavelength that is reflected by viable cultured cells contained in the sample of the cell culture;
   ii) a cuvette for containing the sample of the cell culture is fluidically coupled to an output of the bio-incubator, is disposed between the spectrometer and the PMT, and is fluidically coupled to an inlet of the incubation station by a further transfer system; and
   iii) when there are cultured cells in the sample, the PMT is configured to absorb less light and generate a smaller current than when cultured cells are absent from the sample.

16. The automated device of claim 1, wherein the pump configured to transfer the cultured cells from the bio-incubator to the incubation station is responsive to receipt of a request for viable mitochondria.

* * * * *